United States Patent [19]

Foote

[11] 4,055,792
[45] Oct. 25, 1977

[54] ELECTRICAL CONTROL SYSTEM FOR AN EXHAUST GAS SENSOR

[75] Inventor: Lawrence R. Foote, Birmingham, Mich.

[73] Assignee: Ford Motor Company, Dearborn, Mich.

[21] Appl. No.: 648,340

[22] Filed: Jan. 12, 1976

Related U.S. Application Data

[62] Division of Ser. No. 484,896, July 1, 1974, Pat. No. 3,946,198.

[51] Int. Cl.² .................. G01R 17/02; F02M 7/00
[52] U.S. Cl. .................................. 323/19; 323/40; 330/103; 330/110
[58] Field of Search .................. 323/16, 19, 40, 75 H; 330/97, 103, 110

[56] References Cited

U.S. PATENT DOCUMENTS

| | | | |
|---|---|---|---|
| 3,248,569 | 4/1966 | Weekes | 330/103 X |
| 3,428,884 | 2/1969 | Nordahl | 323/19 |
| 3,493,784 | 2/1970 | Brolin | 330/110 UX |
| 3,688,581 | 9/1972 | Quernec | 323/75 H |
| 3,701,036 | 10/1972 | Stefenel | 330/110 X |

Primary Examiner—A. D. Pellinen
Attorney, Agent, or Firm—Robert A. Benziger; Keith L. Zerschling

[57] ABSTRACT

A system for controlling the application of heat energy to a ceramic exhaust gas sensor and for linearizing the output signal from the sensor. The system compares, electrically, the resistance of a conductive heater winding against a fixed reference and permits a flow of electrical current through the heater whenever the comparison indicates that the temperature of the heater is below the desired level. By periodically establishing a flow of electrical energy through the heater and terminating that flow whenever the heater temperature reaches the desired level, the temperature of the heater may be held at the desired level with great accuracy. In order to periodically reestablish the flow of electrical energy through the heater, the system further provides an oscillator arranged to reestablish current flow through the heater a fixed time period following termination of current flow through the heater. The system also provides a linearizing amplifier connected to the sensor to provide an output signal which is linear with respect to changes in the air/fuel ratio of the mixture being combusted.

1 Claim, 5 Drawing Figures

ELECTRICAL CONTROL SYSTEM FOR AN EXHAUST GAS SENSOR

This is a division of application Ser. No. 484,896, filed July 1, 1974, now U.S. Pat. No. 3,946,198.

CROSS-REFERENCE TO RELATED APPLICATION

This application is related to copending commonly assigned patent application Ser. No. 483,723 filed June 27, 1974 in the names of Gordon L. Beaudoin et al. and titled "Exhaust Gas Sensor Probe, now U.S. Pat. No. 3,936,794".

BACKGROUND OF THE INVENTION

1. Field of the Invention

The present invention is directed to the field of internal combustion engine control systems and primarily to that portion of the above-noted field which is concerned with the chemical analysis of the composition of the exhaust gases produced by the internal combustion engine. More particularly, the present invention is concerned with an electrical system for maintaining the temperature of an exhaust gas sensor at a closely controlled value so that signals produced by the sensor may be accurately and reliably related to the concentration of oxygen in the exhaust gases. The present invention is also concerned with a system for providing an exhaust gas sensor output signal which is linear with respect to changes in the air/fuel ratio of the combustible mixture being provided to the engine and producing the exhaust gas environment of the sensor.

2. Description of the Prior Art

Ceramic sensors for electrically reacting to the partial pressure of oxygen within the exhaust gases produced by an internal combustion engine are known. One such sensor is described in copending, commonly assigned patent application Ser. No. 391,424 —"Method of Manufacture of an Exhaust Gas Sensor for an Air Fuel Ratio Sensing System", now U.S. Pat. No. 3,893,230 and filed in the names of H. L. Stadler et al. The sensor there described relies upon changes in the electrical resistance of titania ceramic material in response to changes in the partial pressure of oxygen in the environment of the sensor. These sensors operate at elevated temperatures on the order of about, for example, 600° to 900° C. Other sensor ceramic materials having a variable electrical resistance are known. Since the resistance of the ceramic material may vary with variations in the temperature within the operating range, as well as with variations in the partial pressure of oxygen, it has become apparent that accurate control of the temperature of the sensor is desirable when partial pressure of oxygen determination is desired.

One prior art system relies upon a platinum heater wire embedded within the ceramic element and an embedded thermocouple operating a control system to maintain a substantially constant flow of electrical current of variable magnitude through the heater wire consonent with maintaining the temperature of the ceramic material at a selected level. By way of example, temperatures of 700° C., plus or minus 2° C are desired so that the electrical resistance of the sensor ceramic may be directly translated into a partial pressure of oxygen for the exhaust gases and, concomitantly, an accurate measure of the air/fuel ratio of the combustion mixture generating the exhaust gases.

This structure, that is, one in which an embedded thermocouple is used to variably control the current through a heater winding, has produced a variety of problems. Firstly, the embedded thermocouple, if it is to be accurate within the desired range of accuracy, is an expensive element. Secondly, the continuous control of a variable flow of electrical current through a heater winding requires expensive electronic or electromechanical components and results in consumption of electrical energy which occurs remote from the sensor and which is wasteful. It is therefore a specific object of the present invention to provide a system for controlling the heating of a wafer of ceramic material which does not require the use of a thermocouple. It is also an object of the present invention to provide such a system which does not dissipate substantial amounts of electrical energy in structures remote from the sensor ceramic. More particularly, it is an object of the present invention to provide such a system which dissipates only minor amounts of electrical energy in components other than the heater.

In the control of an internal combustion engine to provide an exhaust gas having a precisely controlled chemical composition for subsequent treatment by exhaust gas treatment devices, the maintenance of the air/fuel ratio of the combustion mixture at a precisely controlled value is of cardinal importance. The known exhaust gas sensor ceramic materials which demonstrate a variable resistance in response to variations in the partial pressure of oxygen in the exhaust gases and which are compatible in terms of response time and life capacity with an automotive environment show a resistance variation such that the logrithm of resistance is approximately linear in terms of variation in air/fuel ratio. In order to provide an output signal for modulating either the air or the fuel content of the air/fuel mixture it is desirable to match the resistance variation of the sensor, the output signal, and the response of the modulating mechanism. It is therefore an object of the present invention to provide an electrical system for generating an exhaust gas sensor output signal which varies approximately linearly with respect to variation of the air/fuel ratio of the combustion mixture. More particularly, it is an object of the present invention to provide an electrical system for converting the normally logrithmic sensor signal to an approximately linear sensor signal for use by a controller having an approximately linear response for small sensor signals for modulating either the air or the fuel content of the combustion mixture.

SUMMARY OF THE PRESENT INVENTION

The present invention provides an electrical circuit for intermittently energizing an electronic switch such that an electrical current will be intermittently applied to a heater wire. Comparison means are provided responsive to the flow of electrical current through the heater wire for comparing the voltage drop across the heater wire with a preselected ratio in output voltage representative of heater wire temperature at a selected level. The present invention also contemplates the implementation of an electronic oscillator responsive to the termination of flow of electrical current through the heater wire to actuate the switch means to the on or conductive mode a selected interval of time thereafter to reinitiate the flow of electrical current to the heater wire.

The present invention also contemplates the provision of electronic means for modulating the magnitude of the current applied to a resistive ceramic exhaust gas sensor so that a voltage signal may be derived therefrom which varies linearly with respect to variations in the air-to-fuel ratio of the combustion mixture producing the exhaust gases of the sensor environment. An electronic comparator is arranged to compare the voltage across the ceramic exhaust gas sensor with an established reference value and is provided with feedback means for varying the voltage signal applied to the comparator by the ceramic exhaust gas sensor thereby modulating the comparator output signal.

DETAILED DESCRIPTION OF THE PREFERRED EMBODIMENT

Figure 1:
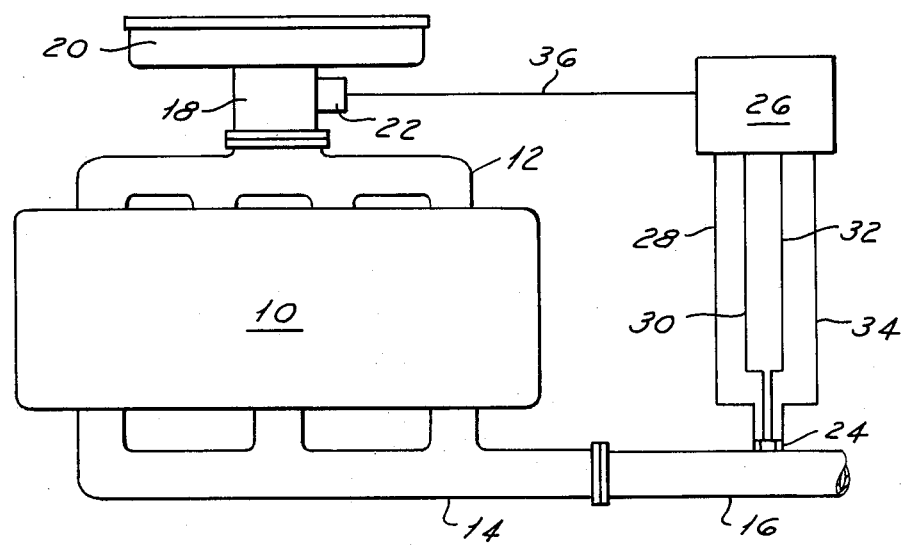
FIG. 1 is a schematic diagram illustrating an internal combustion engine having an exhaust responsive feedback fuel control mechanism with which the present invention is of utility.

Referring now to FIG. 1, an internal combustion engine 10 is illustrated. Internal combustion engine 10 is provided with an intake manifold 12 and an exhaust manifold 14. Exhaust manifold 14 communicates with an exhaust gas conduit 16. A fuel metering and delivery device 18, which may be for example a fuel injection system or a carburetor is illustrated schematically communicating with the intake end of intake manifold 12. Fuel metering and delivery device 18 is provided with an air cleaner 20 such that air injected by engine 10 through intake manifold 12 may be drawn from the atmosphere through air cleaner 20 and through at least a portion of the fuel metering and delivery device 18. Fuel metering and delivery device 18 is further provided with an air/fuel ratio modulator means 22. Air/fuel ratio modulator means 22 may be for example, in the case of an electronic fuel injection system, a variable resistor arranged to control the quantity of fuel delivered to engine 10 in relation to a given quantity of air or, in the case of a carburetor, may be a variably positionable metering orifice arranged to control the quantity of fuel delivered to engine 10 in respect of a given quantity of air. The air/fuel ratio modulator means 22 may alternatively be arranged to control a variably positionable air valve so that the quantity of air injected by engine 10 in respect of a given quantity of fuel delivered by fuel metering and delivery device 18 may be modulated.

Exhaust gas conduit 16 is provided with an exhaust gas sensor 24 which is mounted to conduit 16 so as to place an exhaust gas chemistry responsive element within the stream of exhaust gases flowing through conduit 16. The presently preferred form of this device is that of a variably resistive ceramic exhaust gas sensor formed of, for example, titania or cobalt monoxide. Other forms of this device are suitable and are contemplated. Electronic control means 26 communicates with exhaust gas sensor 24 through a plurality of sensing leads 28, 30, 34 and heater power lead 32. Electronic control means also communicates with the air/fuel ratio modulator means 22 over conductive lead 36. As described hereinbelow, the electronic control means 26 is arranged to respond to changes in the exhaust gas chemistry sensed by exhaust gas sensor 24 to provide a control signal for receipt by air/fuel ratio modulator means 22 which control signal may be arranged to modulate either the fuel or the air content of the air/fuel ratio mixture being provided to internal combustion engine 10 to maintain a desired exhaust gas chemistry.

Figure 2:
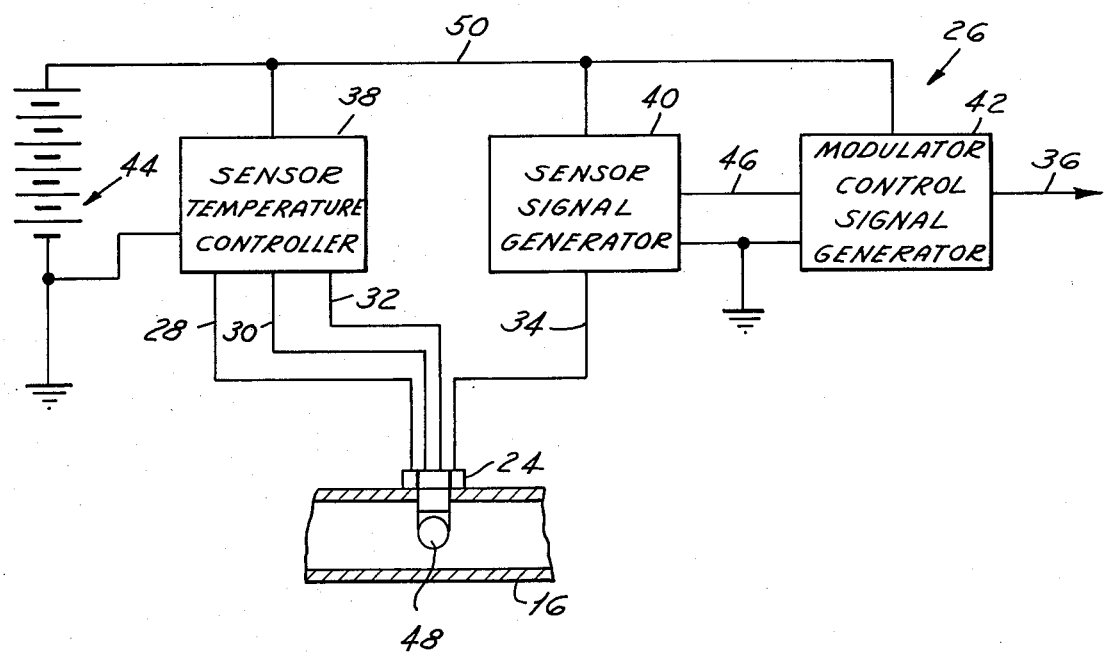
FIG. 2 illustrates, in a block diagram form, the electronic fuel control feedback circuit of the present invention.

Referring now to FIG. 2, electronic control means 26 is shown in a block diagram form. Electronic control means 26 is comprised of sensor temperature controller 38, the sensor signal generator 40 and the modulator control signal generator 42. These devices are energized by a source of electrical energy which may be for example battery 44 or any convenient source of electrical energy. As here illustrated, battery 44 is electrically connected so that its negative terminal is grounded and this corresponds to the present conventional automotive implementation wherein the chassis and body of the vehicle provide a negative common ground. Sensor temperature controller 38 communicates with exhaust gas sensor 24 through leads 28, 30 and 32 while sensor signal generator 40 communicates with sensor 24 through lead 34. The signal from sensor signal generator 40 is communicated to the modulator control signal generator 42 by conducting lead 46.

As illustrated in FIG. 2, exhaust gas sensor 24 is arranged to support a wafer 48 of ceramic sensor material within the exhaust gas stream flowing within exhaust conduit 16. Such structure is disclosed, for example in co-pending commonly assigned patent application Ser. No. 483,723 filed in the names of Gordon L. Beaudoin et al. and titled "Exhaust Gas Sensor Probe", now U.S. Pat. No. 3,936,794. The sensor temperature controller 38, sensor signal generator 40 and modulator control signal generator 42 are illustrated as receiving positive voltage from battery 44 through positive bus or conductor 50.

Figure 3:
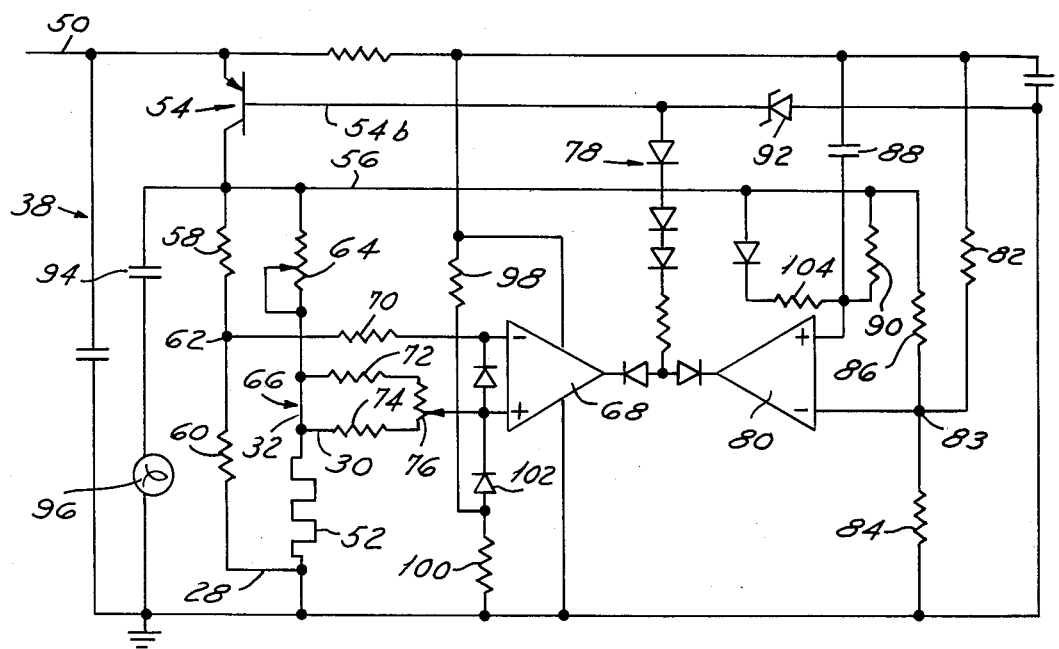
FIG. 3 is an electronic circuit diagram illustrating one aspect of the instant invention.

Referring now to FIG. 3, the sensor temperature controller 38 according to the present invention is illustrated in its presently preferred electronic embodiment. In view of the fact that resistive type ceramic exhaust gas sensors have a resistance value which varies both as a function of temperature and as a function of the partial pressure of oxygen within the gas of the environment of the sensor it is necessary to maintain the sensor at a substantially constant temperature so that resistance variations of the sensor are indicative solely of the partial pressure of oxygen within the exhaust gases and hence of the complete chemistry of the exhaust gases. To this end, a heating means usually in the form of a heater wire is arranged in close proximity to the sensor element per se in order to establish and maintain a fixed level of temperature. The above noted co-pending commonly assigned patent application Ser. No. 483,723 to Gordon L. Beaudoin et al., now U.S. Pat. No. 3,936,794 illustrates one construction wherein the heater wire comprises a coil of platinum resistance wire in surrounding relation to the active ceramic sensor element. In this embodiment, the heater means is denoted as the winding 52 of resistance wire. Power is applied to the circuit of FIG. 3 from the positive bus 50 through transistor switch 54. Transistor switch 54 is illustrated as a PNP transistor having its emitter connected to positive bus 50 and its collector connected to a common conductor 56. Common conductor 56 is provided with a first voltage divider network comprising resistances 58, 60 and having a common point 62. Common conductor 56 is also connected to a second voltage divider comprised of adjustable resistance 64 and heater winding 52. A junction 66 is formed intermediate variable resistance 64 and heater winding 52. Common point 62 is connected to the negative terminal of amplifier 68 through resistance 70. Junction 66 is connected to the positive terminal of amplifier 70 through a pair of fixed trim resistors 72, 74 and adjustable trim resistor 76. The output of amplifier 68 is communicated to the base of transistor switch 54 through diode output network 78.

Oscillator amplifier 80 is arranged to have its output connected to the diode output network 78. The negative terminal of amplifier 80 is communicated to the junction 83 of a voltage divider network comprising resistances 82, 84 connected in series and resistance 86 connected between junction 83 and common conductor 56. The positive terminal of amplifier 80 is connected to one plate of capacitor 88 and, through resistance 90 to common conductor 56.

In addition, the circuit of FIG. 3 illustrates various electronic components such as zener diode 92 which is operative to turn on transistor switch 54 in order to pass voltage spikes and capacitor 94 in series with indicator lamp 96 connected between the common conductor 56 and ground which may be operative to give an indication that the circuit is operational. Furthermore, various other components are illustrated, though not identified, in order to assure that the circuit will turn on and turn off properly and that various voltage levels which may exist within the circuitry will not be of sufficient magnitude to cause damage to the delicate electronic components connected thereto.

The circuit of FIG. 3 maintains control of the temperature of heater 52 by regulating heater resistance. The heater, which may be for example platinum conductive wire, has a high temperature coefficient of resistance, which makes its resistance change to temperature a convenient control variable. With transistor switch 54 in the on, or conductive, mode full bus voltage is applied to the series connection of adjustable resistance 64 and heater winding 52. Transistor switch 54 is maintained in the on or conductive mode by amplifier 68 which draws current through the base lead 54b of transistor 54. As current continuous to flow through winding 52, the resistance of winding 52 will increase with increasing temperature causing the voltage appearing at junction 66 to increase relative to ground. When the heater resistance rises to the value corresponding to the set value, that is the value when the voltage at junction 66 equals to that at common point 62, the voltage at the positive terminal of amplifier 68 will equal the voltage at the negative terminal of the amplifier and the voltage at the output terminal of the amplifier will rise to a high value approximating that on bus 50. Thus, base current will not be allowed to flow out of the base terminal of the transistor 54 and the voltage on common conductor 56 will approach the ground or zero value. The voltage established by voltage divider 98, 100 operating through diode 102 will maintain the bias of the positive terminal of amplifier 68 sufficiently high to hold the switch 54 in the off or non-conducting mode.

Resistances 82, 84, 86 provide a voltage divider applied to the negative input of amplifier 80. This voltage may be for example about 8 volts with 12 volts applied across the bus and ground and with common conductor 56 also at a positive 12 voltage through transistor switch 54. Conversely, as common conductor 56 approaches ground potential, the voltage appearing at the negative input of amplifier 80 will drop to approximately 4 volts under the same conditions. Capacitor 88 in conjunction with resistances 90 and 104 forms an RC oscillatory circuit such that the positive terminal of amplifier 80 will be held at about 10 volts which value will decay to approximately 4 volts as capacitor 88 is charged through resistance 90. The output of amplifier 80 will remain high during this time period and will switch to a low value when the voltage at the positive terminal goes below the 4 volt value established at the negative terminal of amplifier 80. When the output of amplifier 80 goes to a low value base current will be drawn from the base 54b of transistor switch 54 and transistor switch 54 will be turned to the on or conducting mode. At this time, current will again flow through the first and second voltage dividers and amplifier 68 will operate to compare the voltage at junction 66 with the voltage appearing at common point 62. Assuming that the temperature of the heater winding 52 has drifted from the set value, the amplifier 68 will provide a relatively low voltage output at its output terminal holding transistor switch 54 in the on or conducting mode until such time as the temperature has risen to the desired value.

Resistance 64 is here shown to be an adjustable resistance since it is desired to accurately match the ratio of resistance 64 to the resistance of the winding 52 to equal the ratio of resistance 58 and resistance 60 to provide for accurate control. In one form, adjustable resistance 64 may be a piece of manganin wire or other very low temperature coefficient of resistance resistor. The wire may be covered with an electrically insulating sleeve and may be made physically a part of the cable of wires extending from sensor temperature controller 38 to exhaust gas sensor 24. The temperature of the environment of winding 52 may be set at the desired value and the terminal of variable resistance 64 may be varied by use of a brass ferrule. The resistance of variable resistor 64 may be adjusted while the heater is powered from a suitable source. The two sensing wires 28, 30 which extend from the heater allow the controller to respond to heater resistance only with negligible temperature dependent on the resistance of the various leads extending to the heater 52. This is important as the heater leads may have a resistance which is on the same order of magnitude as resistance of the heater itself. The voltage drop from the heater winding to ground is eliminated by sensing lead 28 which places this lead voltage drop outside the comparison bridge. The voltage drop to the heater itself is compensated for by the potential divider composed of resistances 72, 74 and 76.

Figure 4:
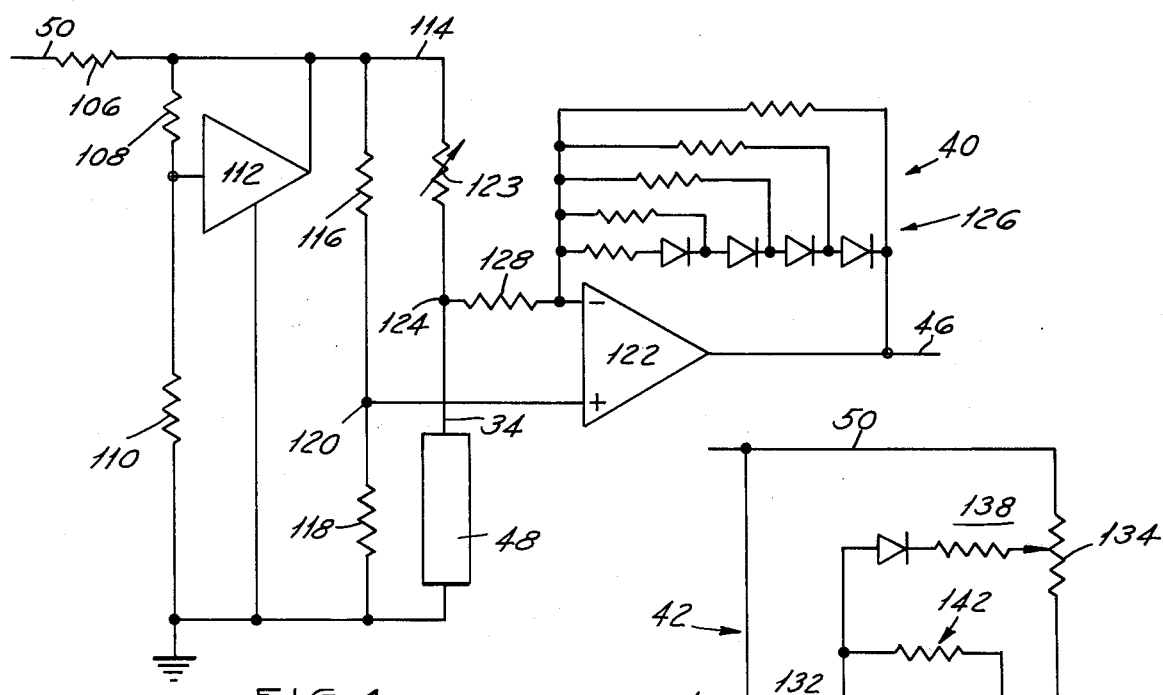
FIG. 4 is an electronic circuit diagram illustrating a second aspect of the present invention.

Referring now to FIG. 4, the sensor signal generator 40 is illustrated. Sensor signal generator 40 receives voltage from common conductor 50. Load resistance 106 is arranged to be in series between common conductor 50 and the remainder of the portion of sensor signal generator 40. The voltage divider comprising resistances 108 and 110 in conjunction with amplifier 112 is operative to provide a regulated voltage bus 114 at about for example 9 volts. A comparison voltage divider is comprised of resistances 116, 118 such that the junction 120 of resistances 116 and 118 is communicated to the positive input terminal of amplifier 122. Sensor 48 is arranged to be excited through lead 34 from variable resistance 123 so that the junction 124 intermediate resistance 123 and sensor 48 is communicated to the negative input terminal of amplifier 122. Amplifier 122 is provided with a linearizing feedback network 126 which interconnects the output of amplifier 122 with the negative input of amplifier 122. The linearizing feedback network 126 is a form of diode function generator. A plurality of diodes, in this instance 4, are connected electrically in series with each other with the cathode of the first diode connected to the output terminal of the amplifier 122 and the anode of the last diode in the series connected electrically in series with a resistor which in turn is connected to one of the inputs to amplifier 122, the input communicating with junction 124. A second resistor is connected electrically in parallel with the series connection of resistor and diodes. A further plurality of electrical resistors are connected to the one input terminal of the amplifier 122 and are arranged to electrically communicate the one input terminal of amplifier 122 with successive anode/cathode junctions of the series connected diodes.

Figure 5:
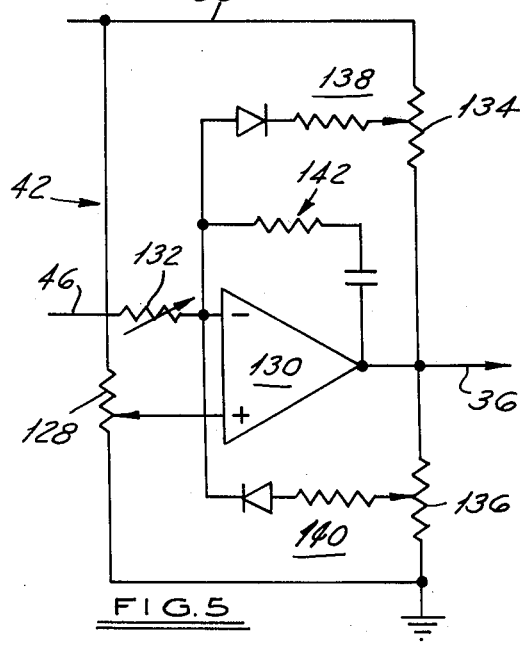
FIG. 5 is an electronic circuit diagram of an air/fuel ratio modulation means usable with the present invention.

Referring now to FIG. 5, the modulator control signal generator 42 is illustrated in a presently preferred embodiment. Signal generator 42 is arranged to receive the signal generated by the sensor signal generator 40 over conductor 46 and is also arranged to receive the positive voltage on bus 50. Potentiometer 128 is connected between bus 50 and ground and is arranged so that its center tab communicates with the positive terminal of amplifier 130. The signal appearing on conductor 46 is applied, through variable resistance 132 to the negative input terminal of amplifier 130. Potentiometer 128 is adjusted so that, when the exhaust gas mixture contains a partial pressure of oxygen indicative of engine operation at the proper air/fuel ratio the signals applied to the positive input terminal of amplifier 130 and on signal lead 46 will be equal in magnitude. Modulator control signal generator 42 is provided with limit signal means 138, 140, which include resistances 134, 136 and which are operative to saturate amplifier 130 for extreme signal conditions and to prevent the application of control signals to the air/fuel ratio modulator means 22 which are of excessive magnitude. Amplifier 130 is also provided with the integrating feedback means 142 which modulates the speed of response of the amplifier 130 to avoid a transient oscillation from building and which integrates air/fuel ratio to provide effectively zero error after sufficient time. Feedback means 142 may be adjusted by use of suitably sized components to provide an integrating time period approaching the internal combustion engine transport time to permit the effects of an error correction signal to be seen by sensor 24.

It will thus be seen that the present invention readily accomplishes its stated objectives. By providing pulse operation of heater winding 52 and by varying the on time of the winding in relation to a predetermined off time, the temperature of the winding may be closely controlled. Furthermore, the substantially full heater winding energization voltage may be applied to heater winding 52 at all times when heating of the winding is desired. The present invention also provides an electronic circuit for generating a sensor output signal which is substantially linear with respect to variations in the air/fuel ratio of the mixture being provided to the internal combustion engine and which is generating the exhaust gases of the environment of the sensor.

I claim:

1. A system for generating an output signal from an exhaust gas sensor which output signal is linear for variations in the air/fuel mixture comprising in combination:

a variable resistance type exhaust gas sensor;

means for generating a regulated voltage;

first voltage divider means, including said sensor, connected to said regulated voltage for generating a signal voltage;

second voltage divider means connected to said regulated voltage in parallel with said first voltage divider means, for generating a reference voltage;

amplifier means having an output terminal and at least two input terminals, said input terminals arranged to receive said signal and reference voltages, respectively; and circuit means interconnecting said output terminal and one of said input terminals, operative to controllably vary the energization of said sensor whereby the output signal of said amplifier may be rendered linear with respect to changes in the air/fuel ratio of the combustion mixture forming the exhaust gas environment of the sensor; said circuit means comprising:

a plurality of diode members connected electrically in series with each other with a first cathode connected to the amplifier means output terminal and a series resistor interconnecting one of the amplifier input terminals to the series connected diode members;

a resistor interconnecting said one amplifier input terminal to the amplifier output terminal in parallel with said series connected resistor and plurality of diode members; and a plurality of resistors, less in number by one than the number of diode members and connected between said one amplifier input terminal and the anode/cathode junctions between selected pairs of the series connected diode members on a one-to-one basis.

* * * * *